United States Patent [19]

van Andel

[11] Patent Number: Plant 6,625

[45] Date of Patent: Feb. 21, 1989

[54] ALSTROEMERIA NAMED STALIBRON

[75] Inventor: Jacob van Andel, Aalsmeer, Netherlands

[73] Assignee: Van Staaveren B.V., Aalsmeer, Netherlands

[21] Appl. No.: 93,876

[22] Filed: Sep. 4, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of Alstroemeria plant particularly characterized by its very large blooms, the outer petals of which are distinguished by a mainly light yellow coloration and having very short streaks of a purplish color at each side of a small notch at the tip of its cuneate petals, the inner petals being of oblong form with aristate tips with numerous deep purplish pencil stripes which spread outwardly from the base of the petals to the petal tips on each side of a longitudinal stripe extending along the centerline of each petal; the upper pair of the inner petals being mainly of a considerably darker coloration than the outer petals and the lower one of the inner petals being substantially the same light yellow color as the outer petals. This plant has substantially the same growth and blooming characteristics as its parent with a profuse and continuous production of flowers from Spring through Fall.

1 Drawing Sheet

BACKGROUND OF THE NEW PLANT

This Alstroemeria clutivar originated as a sport of the variety 'Stalbel' (U.S. plant patent application Ser. No. 872,869 filed June 11, 1986) discovered in 1985 in applicant's greenhouse at Aalsmeer, Holland, and was selected for propagation because of its novel and different coloration and flower form than its parent variety and was reproduced asexually by me and under my direction from its own roots with such satisfactory results that asexual propagation was continued through several successive generations, by division of its rhizomes, which conclusively demonstrated that its novel characteristics would hold true from generation to generation and appeared to be firmly fixed.

DESCRIPTION OF THE DRAWING

My new Alstroemeria cultivar is illustrated by the accompanying photographic drawing which, in full color, shows flowers of a blooming umbel of the plant and demonstrates the unique and distinctive coloration and form of the flowers, the color rendition bearing as nearly true to that specified herein as is possible to obtain by conventional photographic procedures.

DESCRIPTION OF THE NEW PLANT

The following is a detailed description of my Alstroemeria cultivar as observed in greenhouse at Aalsmeer, The Netherlands, the color designations being according to The R.H.S. Colour Chart of The Royal Horticultural Society of London, England.

THE PLANT

Origin: Sport.

Parentage: The variety 'Stalbel' (U.S. plant patent application Ser. No. 872,869 filed June 11, 1986).

Classification: Alstroemeria clone. Form: Erect and tall bush. Height: About 180 cm.

Main stem length: About 180 cm. with flower bearing branches in simple umbel arrangement at its top.

Growth: Strong, vigorous and upright.

Growth rate: Rapid.

Foliage:

*Quantity.*—Abundant.

*Number of leaves.*—Varying as the season progresses.

*Leaf size.*—Large.

*Leaf shape.*—Generally elliptic with entire margins.

*Color.*—Upper side — Middle green. Under side — Grey/Green.

Rhizomes:

*Size.*—Varying with age of plant.

*Color.*—White.

THE BUD

Form: Pear shaped.

Size: Normal.

*Diameter.*—About 2 cm.

*Length.*—About 4 cm.

Color of petals:

*As they begin to unfurl.*—Pale Yellow.

Calyx: This plant has no calyx, the six petals of the flower being perianth and dividing simultaneously.

Peduncle:

*Length.*—Up to about 16 cm.

*Character.*—Erect.

*Color.*—Green.

THE FLOWER

Blooming habit: Continuous and profuse from Spring through Fall.

Size: Very large.

*Diameter.*—About 6.5 to 7 cm.

*Depth.*—About 6 cm.

Borne: Singly.

Shape: Cup-shaped with petal tips tending to curve downwardly.

Petalage:

*Number of petals.*—Six.

*Arrangement.*—Two concentric groups of three.

*Form.*—Outer petals — Ovate with slightly emarginate tip and entire undulate margins. Inner petals — Oblong with aristate tips.

*Texture.*—Soft.

*Appearance.*—Satiny.

*Color.*—Outer petals: Pale Yellow, 12 C, over entire body except for 51 C at the tips and with very short Purplish pencil stripes at the petal tips. Inner petals: Upper pair of oblong form with mucronate tip with lengths longer than the outer petals with two-thirds of the area above the base being a darker Yellow of about 14 B and the outer third being 12 C; the lower one of the inner petals being somewhat shorter than the upper pair and being of substantially the same light Yellow, 12 C, as the outer petals, the lower petal also having some longitudinally-extending pencil stripes.

Peduncle:

*Length.*—About 2 cm.

*Character.*—Strong.

*Color.*—Light Green.

Persistence: The flowers hang on and dry.

Fragrance: None.

Lasting Quality: About twenty days on the plant and about fourteen days as a cut flower in vase keeping.

THE REPRODUCTIVE ORGANS

Stamens:

*Number.*—Six.

*Arrangement.*—Normal.

*Anthers.*—Size: About 8 mm. Color: Grey/Green.

*Filaments.*—Length: About 35 mm. Color: White at base; pink at top.

*Pollen.*—Color: Yellow.

Pistils:

*Number.*—One.

*Style.*—Length: About 3 mm. Color: White at base; pink at top.

*Stigma.*—Color: Violet.

Character of ovaries: Normal.

This new plant differs from its parent 'Stalbel' mainly in flower color and flower shape.

I claim:

1. The new and distinctive Alstroemeria cultivar and the parts thereof, substantially as herein shown and described, characterized by its very large blossoms having light yellow outer petals of ovate form with inner petals of oblong form with aristate tips and heavily marked with purplish pencil stripes, the upper pair being mainly of a darker yellow coloration than the outer petals.

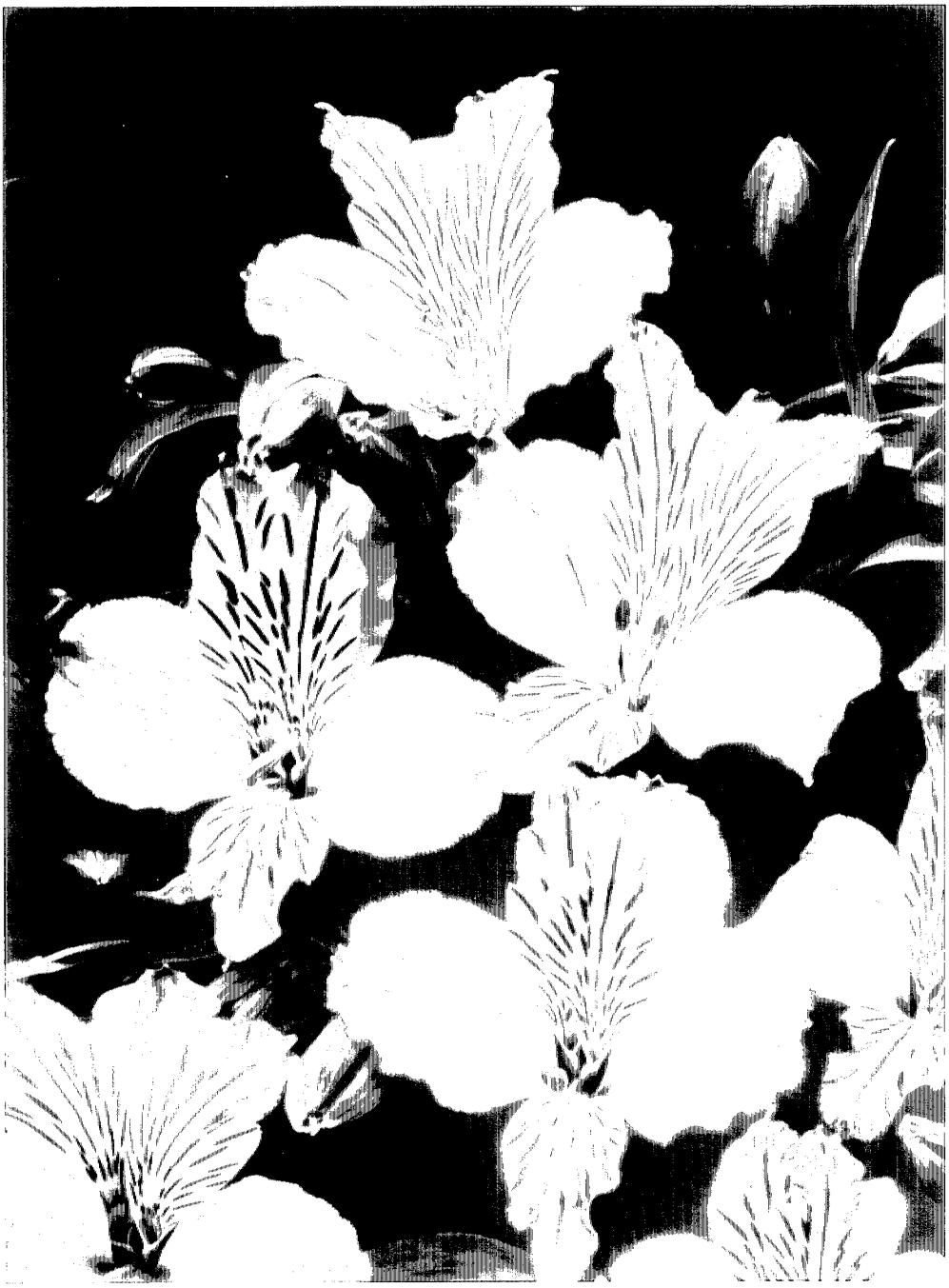

* * * * *